United States Patent [19]

Oki et al.

[11] Patent Number: 4,940,528
[45] Date of Patent: Jul. 10, 1990

[54] OXYGEN SENSOR ELEMENTS

[75] Inventors: Shuichiro Oki, Aichi; Fujio Ishiguro, Nagoya, both of Japan

[73] Assignee: NGK Insulators, Ltd., Japan

[21] Appl. No.: 293,969

[22] Filed: Jan. 6, 1989

[30] Foreign Application Priority Data

Jan. 18, 1988 [JP] Japan .................................. 63-8149

[51] Int. Cl.$^5$ .......................................... G01N 27/409
[52] U.S. Cl. .................................... 204/427; 204/426; 204/428
[58] Field of Search ............... 204/424, 425, 426, 427, 204/428, 429, 15

[56] References Cited

U.S. PATENT DOCUMENTS

| 3,503,809 | 3/1970 | Spacil | 204/427 X |
| 3,843,400 | 10/1974 | Radford et al. | 204/427 X |
| 4,789,561 | 12/1988 | Schaefer et al. | 204/424 X |

FOREIGN PATENT DOCUMENTS 68494 6/1977 Japan .

Primary Examiner—G. L. Kaplan
Attorney, Agent, or Firm—Arnold, White & Durkee

[57] ABSTRACT

An oxygen sensor element including an oxygen ion conductive solid electrolyte body, and electrode layers formed on opposite surfaces of the oxygen ion conductive solid electrolyte body. The electrode layers are mainly constituted by a platinum group metal in which a refractory material is dispersed.

9 Claims, 4 Drawing Sheets

FIG_1
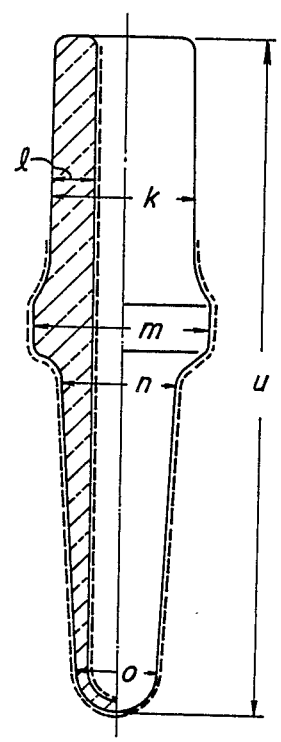

FIG_2a
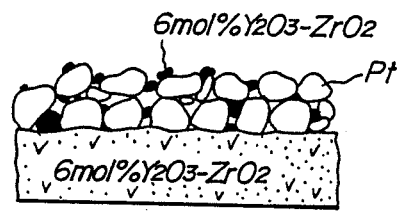
FIG_2b
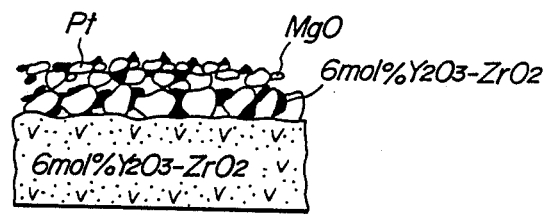
FIG_2c
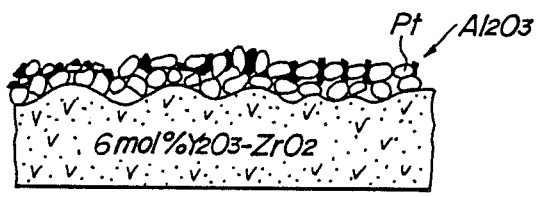

FIG_3
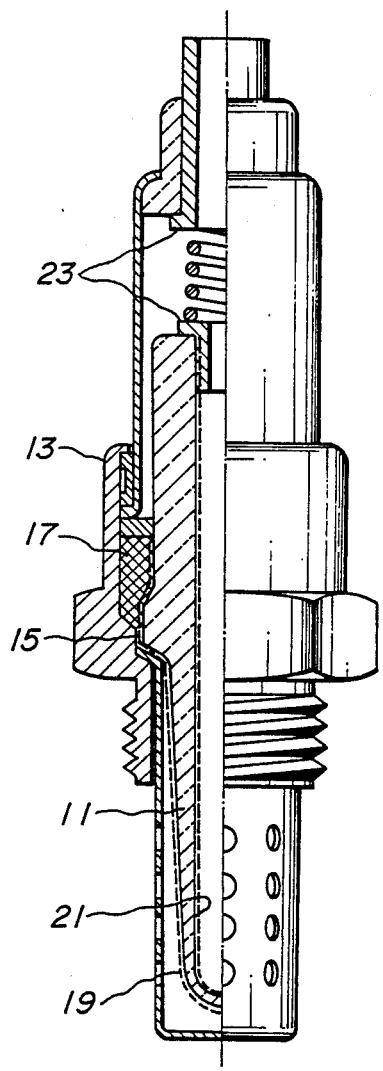

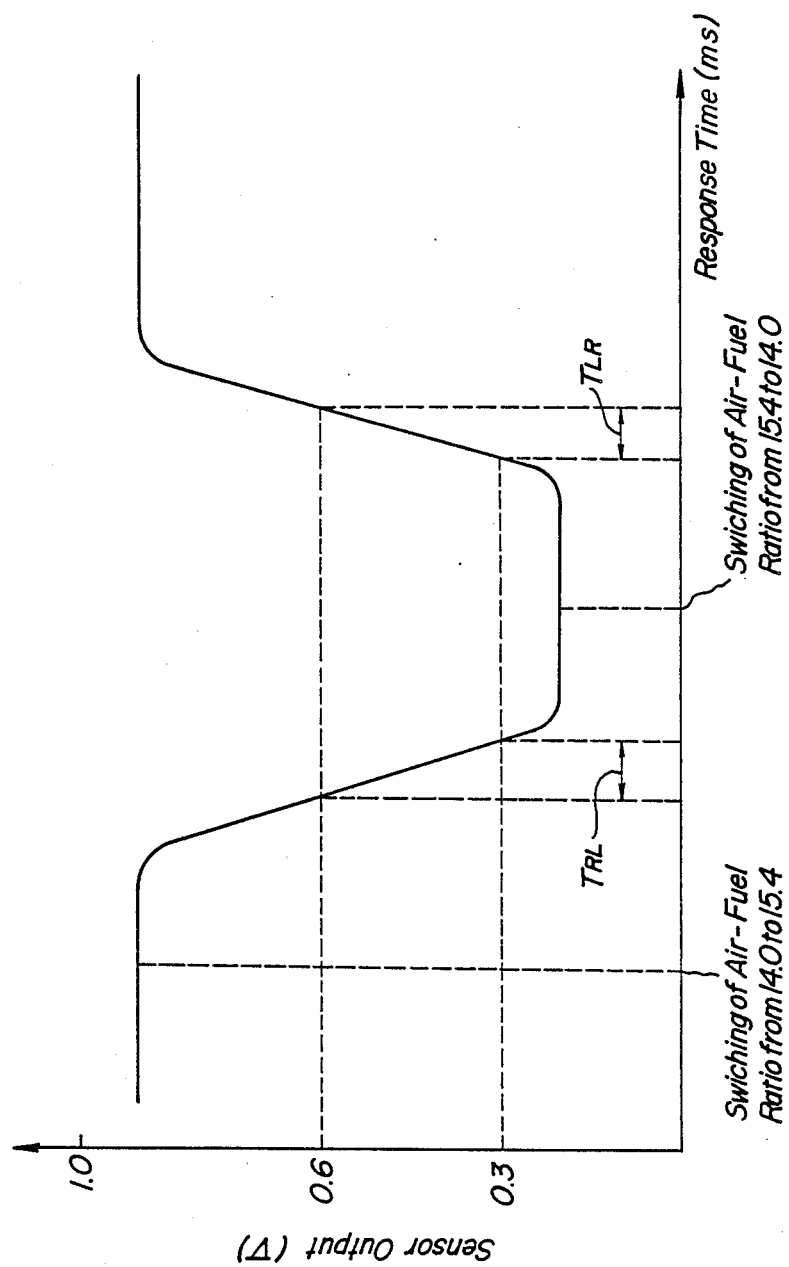

OXYGEN SENSOR ELEMENTS

BACKGROUND OF THE INVENTION

1. Field of the Invention:

The present invention relates to an improvement of oxygen sensor elements, and more particularly the invention relates to oxygen sensor elements having an electrode composition which especially possesses improved gas permeability, gas response characteristics, and durability.

2. Related Art Statement:

Heretofore, oxygen sensors have been used for measuring concentrations of oxygen in exhaust gases from internal combustion engines or the like on the principle of an oxygen concentration cell with the use of an oxygen ion conductive solid electrolyte.

Such oxygen sensors are ordinarily constituted such that a cylindrical bottom-closed shape of an yttria-added zirconia ceramic or the like is used as an oxygen ion conductive solid electrolyte, e.g., electrodes made of platinum are formed on the inner and outer surfaces of the solid electrolyte, and the inner surface electrode is communicated, as a reference oxygen concentration electrode, with open air while the outer surface electrode is exposed, as a measuring electrode, to exhaust gases to be measured. Thus, the concentration of oxygen in the exhaust gases can be measured based on output voltages from the oxygen sensor.

However, electrodes of such an oxygen sensor element to be used in the oxygen sensor of this type are formed by, for example, chemical plating, or physical vapor depositing, in a filmy fashion in a thickness of as thin as several $\mu$m. Therefore, the electrodes have poor gas permeability and bad gas response. In order to improve the response characteristics, heating is employed. However, such a heating technique has problems that the electrodes made of platinum or the like are sintered, catalytic activity drops, adhesion of the electrodes to the substrate becomes poor, the number of three phase points mentioned later decreases, and low temperature operability is deteriorated.

Recently, it has become necessary that oxygen sensors withstand several uses, and possess longer use life under more severe conditions than before. It is desired that electrodes to be used in such oxygen sensors have high gas permeability leading to response characteristic, and greater surface area and high catalytic activity leading to low temperature operability, and that these characteristics are not deteriorated; that is, the electrodes have excellent durability. Furthermore, since conventional electrodes are easily sintered or abraded during exposure to high temperature exhaust gases in their operation, their catalytic activities are damaged, and electric conductivity is deteriorated. Thus, such electrodes cannot satisfy the above-mentioned requisites.

On the other hand, in order to improve durability (adhesion), Japanese Patent Publication No. 45-30,617 discloses an oxygen sensor element in which a porous supporting layer is provided in a thickness of around 100 $\mu$m between a solid electrolyte and an electrode.

However, although this electrode has good durability due to its increased layer thickness, the electrode has the shortcoming that its response characteristic becomes poor because penetrating or exchanging of a gas to be measured through the electrode layer takes a long time. For this reason, the thickness of such an electrode must generally be limited to around several $\mu$m so that sufficient gas permeability or response characteristic may be obtained.

However, since the electrode having such a thickness is filmy, the oxygen sensor element has the problem that the gas permeability thereof or its response characteristic is not so excellent, and that when actually exposed to high temperature exhaust gases, the electrode is likely to be sintered.

SUMMARY OF THE INVENTION

It is an object of the present invention to improve the above-mentioned oxygen sensors, and to provide oxygen sensor elements in which measuring electrodes have enhanced gas permeability and improved low temperature operability and of which the gas response characteristic and durability are improved.

That is, the oxygen sensor according to the present invention has electrode layers formed on an oxygen ion conductive solid electrolyte, and is characterized in that each of the electrode layers is composed mainly of a platinum group metal in which a refractory material is dispersed.

It is preferable that the particle diameter of fine particles of the refractory material in the electrode layer is smaller than the thickness of the electrode layer.

It is more preferable that the thickness of the electrode layer is not more than 5 $\mu$m.

Since the refractory material is dispersed into the platinum group metal in the present invention, fine pores (for instance, 0.1 to 1.0 $\mu$m in diameter) can be formed by thermally treating the electrode. As the reason why the fine pores are formed, one of the factors therefor is considered to be that the refractory material has poor adhesion to the platinum group metal. From this point of view, it is preferable to use a refractory material having poor adhesion to the platinum group metal. Since a number of the fine pores are formed in the electrode, a gas permeability is improved so that the response characteristic is enhanced. In addition, since the refractory material has the function to prevent the platinum group metal from being sintered even when the oxygen sensor element is used in exhaust gases at high temperatures, not only low temperature operability can be improved, but also durability is enhanced. Moreover, an electrode-poisonous material is prevented from reaching or being adsorbed onto three phase points at which the electrode, the solid electrolyte and the gas contact one another by a trapping action against the poisonous material of, for instance, the pores formed by the refractory material or the refractory material itself. This is one of the factors to improve durability. In this case, a material such as Si, Pb, Mn, Zn, P, or S or a compound thereof may be recited as the poisonous material.

In order to improve the trapping action, it is preferable to use a refractory material having a fine particle diameter or a greater surface area.

The reason why the particle diameter of the fine particles of the refractory material is made smaller than the thickness of the electrode is considered as follows:

If the diameter of the particles is greater than the thickness of the electrode to the contrary, the number of the particles or the refractory material coming out from the surface of the electrode becomes greater. Consequently, the sintering of the electrode material having poor adhesion proceeds during thermal treatment while bypassing the particles. Thus, fine particles are considered difficult to be formed. This reduces the internal resistance, and does not attain improvement of the response characteristic as desired. Therefore, the diameter of the fine particles preferably falls within the range from about 0.05 to 3 μm, more preferably in a range from 0.3 to 1.0 μm. When such fine particles are used, it is unnecessary to increase the thickness of the electrode so as to improve durability. Thus, gas permeability is not damaged, or the performances of the electrode are not deteriorated. The thickness of the electrode is preferably not more than 5 μm from the standpoint of durability and easiness of forming open pores.

These and other objects, features, and advantages of the invention will be appreciated upon reading the following description of the invention when taken in conjunction with the attached drawings, with the understanding that some modifications, variations, and changes of the same could be made by the skilled person in the art to which the invention pertains without departing from the spirit of the invention or the scope of claims appended hereto.

BRIEF DESCRIPTION OF THE ATTACHED DRAWINGS

For a better understanding of the invention, reference is made to the attached drawings, wherein:

FIG. 1 is a partially sectional view of an embodiment of the oxygen sensor element according to the present invention;

FIGS. 2a, 2b and 2c are schematic views of particle structures of electrodes;

FIG. 3 is a partially sectional view of an oxygen sensor element assembled into a housing; and FIG. 4 is a diagram illustrating a principle of measurement of the response characteristic.

DETAILED DESCRIPTION OF THE INVENTION

The present invention will be explained in more detail below.

Any material may be employed as the solid electrolyte used in the present invention so long as it is oxygen ion conductive. For instance, $ZrO_2$ containing $Yb_2O_3$, $Sc_2O_3$, $Y_2O_3$, $CaO$, $MgO$, $ThO_2$, or $CeO_2$, $CeO_2$ containing $CaO$ or $La_2O_3$, $Bi_2O_3$ containing $Er_2O_3$ or $SrO$, and $ThO_2$ containing $Y_2O_3$ may be recited. Particularly, $ZrO_2$ containing $Y_2O_3$ (fully stabilized and partially stabilized zirconia) is preferred.

As the configuration of the solid electrolyte element made of the above-mentioned solid electrolyte, a bottom-closed cylindrical shape having a projecting or recessed band at a portion of the outer surface thereof which is to be brought into contact with exhaust gases is particularly advantageously suited. Since NGK Insulators, Ltd. proposed solid electrolyte elements having such a shape in detail in Japanese Utility Model Publication No. 61-8,359, a detailed explanation thereof is omitted.

Electrodes are provided by forming a metallic layer on each of inner and outer surfaces of the solid electrolyte having the bottom-closed cylindrical shape. In the present invention, such an electrode may be formed by using a conventional technique.

As the conventional technique, there are available a chemical process such as electroless plating or chemical vapor deposition, a physical process such as evaporation, sputtering, or ion plating, a screen printing process, or a coating process by using a chloride such as chloroplatinic acid or rhodium chloride, or a nitric acid compound (in air or in a reducing atmosphere). When the conventional technique is to be applied, it is needless to say that a preliminary treatment such as washing or etching of a portion of the solid electrolyte at which an electrode layer is to be formed is preferably done, if necessary. Further, as a matter of course, any of the conventional techniques may be combined together.

It is preferable to disperse fine particles of the refractory material into the electrode layer simultaneously with the film formation of the electrode layer, because the electrode layer having particularly excellent uniformity and durability can be obtained in such a case. For this purpose, for example, in the case of the evaporating process, a vaporizing source such as a platinum group metal or an alloy consisting mainly of such a metal and another evaporating source for dispersing refractory fine particles in a film to be formed are prepared, which are simultaneously evaporated. A desired electrode layer can similarly be formed by using other processes.

Then, gas permeability, durability, and adhesion of the thus formed electrode layer can be improved by thermal treatment under specific conditions.

As to the above-mentioned finely particulate refractory material, any material may be employed so long as it has a melting point of not less than 1,000° C. or around 1,000° C., is relatively stable against oxidation and reduction, and is difficult to make solid solution with the platinum group metal as the material of the electrode or is slightly solid solved thereinto. For instant, $Al_2O_3$, $BaO$, $BeO$, $B$, $BN$, $BC$, $Ce$, $CeO_2$, $Cr_2O_3$, $Cr$, $Fe$, $FeO$, $CaO$, $Co$, $CoO$, $C$, $La_2O_3$, $MgO$, $MnO$, $Mo$, $SiO_2$, $SiC$, $SrO$, $Th$, $ThO_2$, $V_2O_3$, $W$, $WO_3$, $ZrO_2$, $Zr$, $TiC$, $ZrSiO_4$, $Y_2O_3$, and $Yb_2O_3$ may be recited.

If the thickness of the electrode layer is less than 0.5 μm, the electrode layer is abraded during operation of the oxygen sensor in an actual measuring atmosphere. Thus, electrical conductivity is likely to become poor, and durability is damaged. To the contrary, if the thickness of the electrode layer is more than 5.0 μm, hollow pores which increase the surface area of the electrode, improve catalyst capability to promote the gas reaction, and enhance the gas permeability, are not easy to form. Accordingly, the thickness of the electrode layer is preferably in a range from 0.5 to 5.0 μm, and more preferably in a range from 0.7 to 3 μm.

The electrode layers are thermally treated in an oxidizing atmosphere such as air, in a neutral atmosphere such as an $N_2$ atmosphere, or in a reducing gas atmosphere containing CO gas, the sintering of the plating material such as Pt is promoted so that pores are formed between the crystal grains to increase the surface area of the plated layer.

Thus, since the electrode having excellent gas permeability and the great surface area is formed on the solid electrolyte, the oxygen sensor element having a speedy gas response characteristic, good low temperature operability, and high durability can be obtained.

Further, Pt is preferred as the material of the electrode. Although Pt is unfavorably likely to be abraded from the standpoint of durability, it favorably has a speedy response characteristic due to its excellent catalytic activity. The shortcoming that Pt is likely to be abraded can be reduced by the technique of the present invention.

As shown in FIG. 1, the electrode layer is formed up to an upper end of the solid electrolyte for the inner surface, and up to a portion above a greater diameter portion for the outer surface. This may be varied depending upon necessity. For instance, it is possible that an electrode layer band is formed on the outer surface of the electrode at a portion above the closed end of the element by about 10 mm, and the greater diameter portion of the element is connected to the electrode layer with a metallic paste-baked layer. At that time, when the metallic paste-baked layer is fired simultaneously with the base solid electrolyte, stronger adhesion is advantageously obtained. Furthermore, since the inner electrode doesn't affect the response characteristic, it may be formed by coating and baking a Pt paste.

Then, a spinel coating layer is formed by plasma spraying spinel grains to protect the electrode as in the conventional technique.

Next, two kinds of the solid electrolyte elements to be used in the present invention will be explained below.

First solid electrolyte elements

First, 5 wt % of $Al_2O_3$ was added and mixed into 94 mol % of $ZrO_2$ and 6 mol % of $Y_2O_3$, which was dried and then calcined at 1,100° C. for 10 hours. The calcined powder was ground with the addition of zirconia grinding media and water for 20 hours by means of a pot mill. After 0.5 wt % of a water-soluble binder was added to the ground powder, the mixture was granulated by a spray drier.

Then, a shaped body was prepared by using the thus granulated powder according to a rubber press and slicing, and the solid electrolyte element was obtained by firing the shaped body at 1,350° C. for 10 hours. Elements thus obtained were used as Sample Nos. 1 through 12 and Sample Nos. 16 through 19 (These samples are shown in Table 2 given later as "$Y_2O_3$—$ZrO_2$").

Second solid electrolyte elements 1 wt % of $SiO_2$ and 1 wt % of $Al_2O_3$ were added to 12 mol % of CaO and 88 mol % of $ZrO_2$, which was mixed, dried, and then calcined at about 900° C. for 10 hours in the same manner as in the case of the first solid electrolyte elements. Each of the thus obtained calcined powders was ground in a pot mill with the addition of zirconia grinding media and water for 20 hours. The ground powder was added with 0.5 wt % of a water-soluble binder, which was granulated by a spray drier. By using the granulated powder, a shaped body was prepared by rubber press and slicing, and fired at 1,550° C. for 10 hours. Thus obtained solid electrolyte elements were used as Sample Nos. 13 through 15 (These samples are shown in Table 2 as "CaO—$ZrO_2$").

Each of the first and second solid electrolyte elements had a shape as shown in FIG. 1 in which dimensions were u=50 mm, m=9 mm, n=6 mm, and O=4 mm, the thickness of the tip portion being 0.7 mm.

Next, electrode layers were formed onto desired portions of each of the first and second electrolyte elements according to one of the electrode layer-forming processes or by appropriately combining them.

The thus obtained samples were subjected to thermal treatment given in Table 2. With respect to each of Sample Nos. 5 through 9, 12 and 15 in Table 2, the surface of the solid electrolyte element was etched with a 5% aqueous solution of hydrofluoric acid (HF) for 15 minutes as a pretreatment for the formation of the electrode layers.

Sample No. 17 in Table 2 possessed a two layer structure consisting of a platinum single layer and a rhodium layer formed on the platinum single layer. This rhodium layer contains 12 wt % of MgO having the average particle diameter of 0.3 μm with respect to rhodium. Sample No. 16 is also of a two layer structure electrode consisting of a platinum single layer and another platinum layer formed on the above platinum single layer, said another platinum layer containing 2 wt % of $Al_2O_3$ having an average particle diameter of 0.1 μm.

Both of Sample Nos. 18 and 19 are Comparative Examples not containing such refractory materials.

With respect to each of all the thus formed Samples, an $MgAl_2O_4$ spinel coat was formed in a thickness of 100 μm on the entire surface of the sample excluding a portion of the outer electrode of the oxygen sensor element under from the greater diameter portion excluding a portion at which the oxygen sensor element contacts a housing.

Results obtained above are shown in the following Tables 1 and 2.

In order to schematically illustrate the typical electrode structure in Table 2, sectional diagrammatic views of Sample Nos. 1, 6 and 16 are shown in FIGS. 2a, 2b and 2c, respectively.

TABLE 1

| Symbol | Refractory material | Particle* diameter (μm) | Dispersed** amount (wt %) |
|---|---|---|---|
| a | $ZrO_2$ added with 6 mol % of $Y_2O_3$ | 0.6 | 6 |
| b | $ZrO_2$ added with 12 mol % of CaO | 0.4 | 6 |
| c | $ZrO_2$ | 0.1 | 20 |
| d | " | 0.2 | 3 |
| e | $Al_2O_3$ | 0.1 | 5 |
| f | " | 0.1 | 2 |
| g | " | 0.5 | 10 |
| h | MgO | 0 3 | 5 |
| i | " | 0.3 | 12 |
| j | BN | 1.2 | 5 |

Note:
*Average particle diameter measured by Laser Diffraction Method
**Dispersed amount (wt %) relative to metallic component

TABLE 2

| | No. | Solid electrolyte | First layer | | | Second layer (formed in the same manner as in first layer) | | |
|---|---|---|---|---|---|---|---|---|
| | | | Metal | Dispersed* powder | Thickness** (μm) | Metal | Dispersed* powder | Thickness** (μm) |
| Present invention | 1 | $Y_2O_3$—$ZrO_2$ | Pt | a | 3.0 | | | |
| | 2 | | " | " | 0.7 | | | |
| | 3 | | " | " | 2.0 | | | |
| | 4 | | " | " | 0.7 | | | |
| | 5 | | " | " | " | Pt | g | 0.5 |
| | 6 | | " | " | " | " | h | 0.6 |
| | 7 | | " | " | " | " | j | 2.0 |

TABLE 2-continued

| | No. | | | | Thickness (μm) | | | | |
|---|---|---|---|---|---|---|---|---|---|
| | 8 | | " | " | " | | | | |
| | 9 | | " | " | " | | | | |
| | 10 | | " | c | 1.2 | | | | |
| | 11 | | " | e | 0.7 | | | | |
| | 12 | | " | " | " | | Rh | h | 0.5 |
| | 13 | CaO—ZrO₂ | " | a | 3.0 | | | | |
| | 14 | | " | " | " | | | | |
| | 15 | | " | b | 0.8 | | Pt | d | 0.5 |
| | 16 | Y₂O₃—ZrO₂ | " | | 0.3 | | | | |
| | 17 | | " | | 0.5 | | Rh | i | 0.6 |
| Comparative Example | 18 | | " | | 0.7 | | | | |
| | 19 | | " | | " | | Rh | | 0.2 |

| | No. | Second layer (formed in a manner different from that of first layer) | | | Thermal treatment | Thickness (μm) | | Remarks |
|---|---|---|---|---|---|---|---|---|
| | | Metal | Dispersed* powder | Thickness** (μm) | | Inside | Outside | |
| Present invention | 1 | | | | 700° C. 30 min. in air | 0.7 | 3.0 | FIG. 2a |
| | 2 | | | | no thermal treatment | 0.9 | 0.7 | |
| | 3 | | | | 700° C., 30 min. in air | " | 2.0 | |
| | 4 | | | | " | 0.7 | 0.7 | |
| | 5 | | | | " | 1.0 | 1.2 | |
| | 6 | | | | " | " | 1.3 | FIG. 2b |
| | 7 | | | | " | " | 2.7 | Inner surface electrode formed by electroless plating |
| | 8 | Pt | h | 1.0 | " | " | 1.7 | |
| | 9 | Rh | " | 0.7 | " | " | 1.4 | |
| | 10 | | | | " | 0.9 | 1.2 | |
| | 11 | | | | " | " | 0.7 | |
| | 12 | | | | " | " | 1.2 | |
| | 13 | | | | 800° C., 3 hr. in reducing atmosphere | 1.0 | 3.0 | |
| | 14 | | | | no thermal treatment | " | 3.0 | |
| | 15 | | | | 700° C., 30 min in air | " | 1.3 | |
| | 16 | Pt | f | 0.7 | " | " | 1.0 | FIG. 2c |
| | 17 | | | | " | " | 1.0 | |
| Comparative Example | 18 | | | | " | 0.6 | 0.7 | |
| | 19 | | | | " | " | 0.9 | |

Note:
*Dispersed powder is denoted by using symbols given in Table 1.
**Thicknesses were determined from SEM photographs.

Next, as shown in FIG. 3, each of the oxygen sensor elements 11 was fitted into a housing 13, and electrical connection was assured. First, the oxygen sensor element 11 was fixed to a stepped portion 15 of the housing 13 with a sealant 17 such as talc. The outer electrode 19 was electrically contacted with the housing 13, and electrically connected to the exterior through the housing 13. The inner electrode 21 was connected to a signal detecting circuit (not shown) outside the sensor element through a central electrode 23.

With respect to the thus constructed oxygen sensors, evaluation tests were conducted for the following characteristics: response characteristic, low temperature operability and durability. For effecting the evaluation tests, the oxygen sensor was attached to an exhaust pipe immediately downstream of an automobile engine and an oxygen partial pressure of an exhaust gas at a maximum temperature of about 1,000° C. was measured.

Response characteristic

While the temperature of the exhaust gas was maintained at 350° C., the air-fuel ratio of the exhaust gas was switched from 14.0 to 15.4 and inversely from 15.4 to 14.0 as shown in FIG. 4 by means of an engine control computer outside a 4 cylinder type gasoline engine having a displacement of 1,500 cc. $T_{RL}$ (ms) during when the output of the sensor varied from 0.6 V to 0.3 V and $T_{LR}$ (ms) during When it varied from 0.3 V to 0.6 V were measured after the switching. Results are shown in Table 3.

Measurement of low temperature operability

The temperature of the exhaust gas from the engine having the displacement of 1,500 cc was lowered from 400° C. to a temperature at which since outputs from the sensor became feeble, feedback control was impossible; that is, the engine stopped. The temperature of the exhaust gas at the engine-stopped time was measured. Results are shown in Table 3.

Measurement of durability

After the durability test in a 2,000 hour life cycle, the above-mentioned response time and low temperature operability were measured. In evaluations, the response time was judged good when it was less than twice that of $T_{RL}$ or $T_{LR}$ (ms) in the initial state. The low temperature operability was judged good when it was lower than that in the initial state by not more than +50° C. Results are shown in Table 3. In each case, the test was conducted with respect to three samples. "O" and "X" in Table 3 denote the case where two or three samples were good, and the case where two or three samples were bad, respectively.

TABLE 3

| No | Response time $T_{RL}$ (ms) | Response time $T_{LR}$ (ms) | Low temperature operability (°C.) | Life cycle after 800 hours Response time | Life cycle after 800 hours Low temperature operability |
|---|---|---|---|---|---|
| Invention product 1 | 120 | 100 | 270 | O | O |
| 2 | 100 | 80 | 300 | O | O |
| 3 | 60 | 40 | 290 | O | O |
| 4 | 45 | 40 | 295 | O | O |
| 5 | 80 | 70 | 265 | O | O |
| 6 | 75 | 85 | 270 | O | O |
| 7 | 70 | 65 | 290 | O | O |
| 8 | 100 | 110 | 250 | O | O |
| 9 | 105 | 135 | 270 | O | O |
| 10 | 80 | 60 | 280 | O | O |
| 11 | 100 | 105 | 275 | O | O |
| 12 | 120 | 110 | 260 | O | O |
| 13 | 150 | 100 | 290 | O | O |
| 14 | 170 | 135 | 300 | O | O |
| 15 | 120 | 65 | 280 | O | O |
| 16 | 40 | 45 | 300 | O | O |
| 17 | 80 | 90 | 270 | O | O |
| Comparative product 18 | 150 | 80 | 350 | x | x |
| 19 | 300 | 380 | 325 | x | x |

As is seen from Table 3, the invention products have more excellent low temperature operability and durability as compared with comparison products.

As is evident from the foregoing explanation, since the electrodes of the oxygen sensor are made of the platinum group metal in which the refractory material is dispersed, sintering of the electrodes can effectively be prevented by the refractory material. Thereby, response and particularly low temperature operability can be made excellent, and contamination of the oxygen sensor with a poisonous material can be prevented. Thus, durability can be improved.

What is claimed is:

1. An oxygen sensor element for measuring oxygen partial pressure in an exhaust gas of an internal combustion engine, said oxygen sensor element comprising: an oxygen ion conductive solid electrolyte body; an electrode layer formed on outer and inner surfaces of said oxygen ion conductive solid electrolyte body; and a protective film formed on the outer electrode layer, at least the outer electrode layer having a thickness of 0.5 to 5.0 μm and consisting essentially of a platinum group metal in which a particulate refractory material is uniformly dispersed simultaneously with the formation of the outer electrode layer, the refractory material having a particle diameter in the range of 0.05 to 3.0 μm, wherein the diameter of said refractory material is not greater than 3.0 μm when the thickness of the outer electrode layer is not less than 3.0 μm and the diameter of said refractory material is not more than a thickness of the electrode layer when the thickness of the electrode layer is not greater than 3.0 μm.

2. The oxygen sensor element according to claim 1, wherein the particle diameter of said refractory material is smaller than the thickness of each of the electrode layers.

3. The oxygen sensor element according to claim 2, wherein the thickness of each of the electrode layers is in the range of 0.5 to 5 μm.

4. The oxygen sensor element according to claim 1, wherein the thickness of each of the electrode layers is not more than 5 μm.

5. The oxygen sensor element according to claim 1, wherein the particle diameter of said refractory material is in the range of 0.3 to 1.0 μm.

6. The oxygen sensor element according to claim 1, wherein the refractory material comprises at least one material selected from the group consisting of $Al_2O_3$, BaO, BeO, B, BN, BC, Ce, $CeO_2$, $Cr_2O_3$, Cr, Fe, FeO, CaO, Co, CoO, C, $La_2O_3$, MgO, MnO, Mo, $SiO_2$, SiC, SrO, Th, $ThO_2$, $V_2O_3$, W, $WO_3$. $ZrO_2$, Zr, TiC, $ZrSiO_4$, $Y_2O_3$, and $Yb_2O_3$, 7. The oxygen sensor element according to claim 1, wherein the electrode layers are thermally treated in a reduction gas atmosphere containing CO.

8. The oxygen sensor element according to claim 1, wherein the solid electrolyte comprises at least one material selected from the group consisting of: $ZrO_2$ containing at least one additive selected from the group consisting of $Yb_2O_3$, $Sc_2O_3$, $Y_2O_3$, CaO, MgO, $ThO_2$, and $CeO_2$; $CeO_2$ containing at least one additive selected from the group consisting of CaO and $La_2O_3$; $Bi_2O_3$ containing at least one additive selected from the group consisting of $Er_2O_3$ and SrO; and $ThO_2$ containing $Y_2O_3$.

9. The oxygen sensor element according to claim 1, further comprising an intermediate electrode layer formed between said oxygen ion conductive solid electrolyte body and the outer electrode layer, said intermediate electrode layer being a platinum group metal.

* * * * *